United States Patent [19]

Bhatt

[11] Patent Number: 4,795,441
[45] Date of Patent: Jan. 3, 1989

[54] MEDICATION ADMINISTRATION SYSTEM

[76] Inventor: Kunjlata M. Bhatt, 4789 Hedgewood, Birmingham, Mich. 48010

[21] Appl. No.: 39,120

[22] Filed: Apr. 16, 1987

[51] Int. Cl.$^4$ ............................................. A61M 1/00
[52] U.S. Cl. ..................................... 604/124; 604/80; 604/191; 604/7; 604/259; 128/DIG. 26; 206/364; 248/231.8
[58] Field of Search ................. 128/DIG. 26; 604/80, 604/82, 83, 181, 191, 258, 259, 410, 7, 56, 81, 110, 111, 183, 186, 124; 206/363–366, 564; 248/231.8, 316.7

[56] References Cited

U.S. PATENT DOCUMENTS

| 2,077,774 | 4/1937 | Rudder | 604/7 |
| 2,278,401 | 3/1942 | Micari | 248/231.8 |
| 2,710,004 | 6/1955 | Stamper | 604/80 |
| 2,839,201 | 6/1958 | Auster | 248/231.8 |
| 2,854,027 | 9/1958 | Kaiser et al. | 604/83 |
| 3,276,472 | 10/1986 | Jinkens et al. | 604/83 |
| 4,044,757 | 8/1977 | McWhorter et al. | 604/82 |
| 4,195,734 | 4/1980 | Boner et al. | 206/564 |
| 4,466,538 | 8/1984 | Gianni | 206/366 |
| 4,467,947 | 8/1984 | Minneman | 206/366 |
| 4,501,363 | 2/1985 | Isbey, Jr. | 206/564 |
| 4,657,138 | 4/1987 | Watson | 206/564 |
| 4,666,429 | 5/1987 | Stone | 604/83 |

FOREIGN PATENT DOCUMENTS 0737249 6/1966 Canada ................................. 604/83

Primary Examiner—Dalton L. Truluck
Assistant Examiner—Denise Whelton
Attorney, Agent, or Firm—Gifford, Groh, Sheridan, Sprinkle and Dolgorukov

[57] ABSTRACT

An improved medication administration system includes a series of one way valves disposed closely adjacent and in direct fluid communication with an auxiliary IV line leading to a patient. A plurality of syringes filled with various selected medications are each secured in a tray against axial and lateral movement by depressing them into correspondingly dimensioned longitudinal grooves. The flanges of the syringes abut a lip of the tray to further restrict axial movement. The nozzles of the syringes are connected to the inlets of the valves so that medication can be adminstered intravenously by simply depressing the appropriate syringe plunger. The tray is surrounded by a supporting outer box which includes retractable clamps for fastening the tray to an operating table. A second similarly shaped box is adapted to be clipped to the first box or clamped to the table. The second box can contain miscellaneous medical equipment.

13 Claims, 3 Drawing Sheets

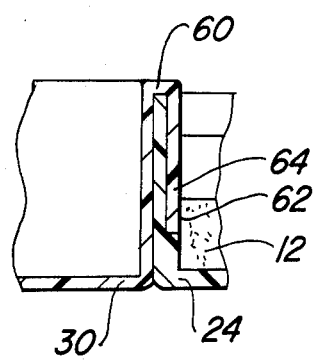
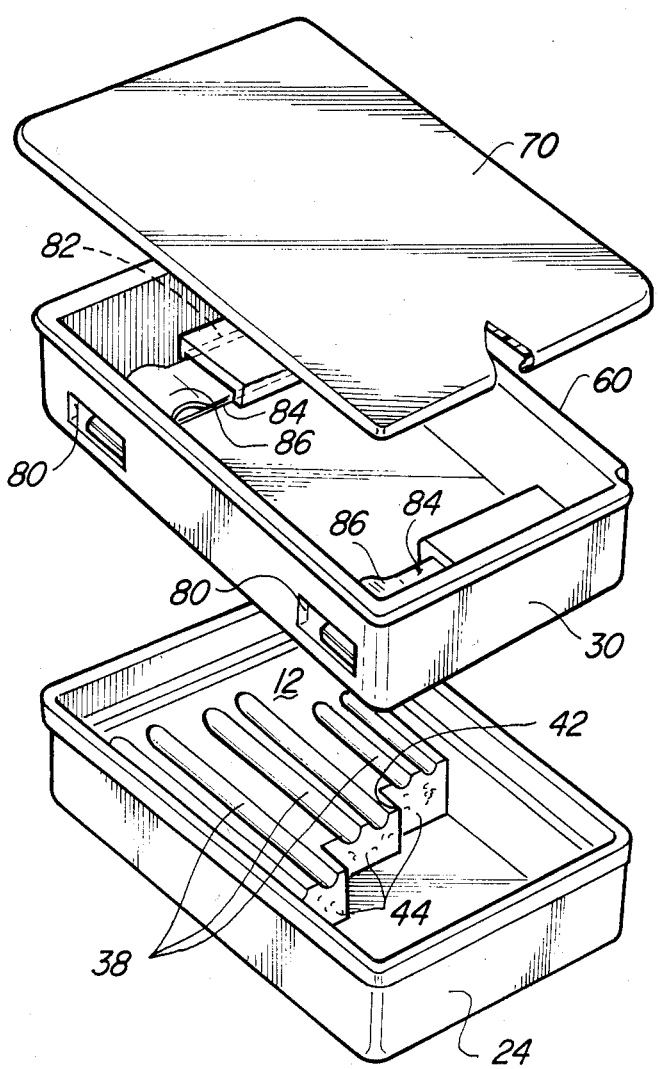
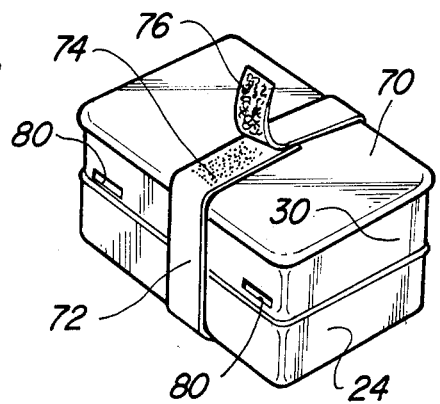
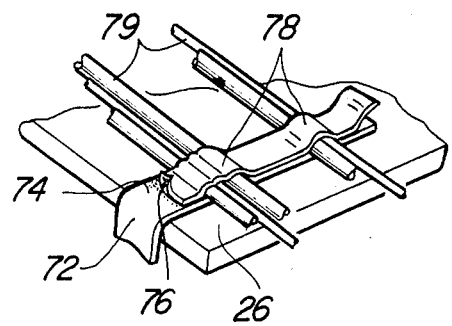

MEDICATION ADMINISTRATION SYSTEM

BACKGROUND OF THE INVENTION

I. Field of the Invention

This invention relates to medication delivery systems and, in particular, to an organized system for the safe delivery of various selected medications to a patient having an intravenous (IV) line in place.

II. Description of the Prior Art

Several previously known medication administration systems are designed to deliver a selected medication intravenously to a patient. In one such system, the medication is contained in a syringe which is attached directly to a needle. The needle is inserted directly into the vein of the patient and the medication is delivered through a bore in the needle.

In patients who are receiving nourishment and/or fluids intravenously, several additional previously known delivery systems have been employed. In these systems an IV line connects the source of fluids to a needle which is inserted into the vein of the patient. The fluids drain by gravity into the patient's circulatory system.

In one administration system for use with such an IV line, medication is injected directly into the source of IV fluid. Medications given in this manner must be compatible with the IV fluid itself, and with other medications previously injected into the source of IV fluids.

Another delivery system, known as intravenous piggyback (IVPB), is used when relatively large volumes of medication are to be added to IV fluids. In this system, a bag or bottle containing the selected medication is arranged to drip gradually into a side port of the IV line, forced by gravity.

Yet another IV administration system employs a valve or stop cock disposed in the IV line intermediate the source of IV fluids and the patient. By connecting a source of medication to the inlet of the valve, the medication can be delivered to the patient by opening the valve.

Each of the above described delivery systems has certain disadvantages. Systems employing needles which are injected into the patient or into the IV fluid directly, involve a risk that the user could accidentally puncture the patient or him or herself if the needle is not carefully handled. Moreover, syringes and needles in combination are susceptible to theft and potential misuse.

More importantly, often times more than one medication must be administered to a patient. This is especially true in the case of an anesthesiologist who is preparing a patient for surgery. In addition, precise control of the blood levels of a given medication depend on the administration of a precise amount at a precise time. The present invention overcomes these and other disadvantages.

SUMMARY OF THE PRESENT INVENTION

The present invention provides for a convenient and organized system for delivery of various selected medications through an IV line to a patient. An auxiliary IV line is connected to a side port of the main IV line and contains a series of valves which permit the addition of medication while preventing back flow of IV fluid. The valves may be three way stop cocks which must be manually opened to administer medication. Preferably, however, they are one way valves which permit the administration of medication without having to open the valve manually. The valves are arranged in or closely adjacent the auxiliary IV line so that there is little or no dead space between the valve outlet and the auxiliary IV line itself.

A number of conventional syringes are filled with various selected medications and are each connected by a nozzle to an inlet of one of the valves. A precise amount of the medication can be delivered by depressing the plunger to deliver the proper volume of medication through the opened valve. The medication is flushed through the system by a second IV fluid source.

To neatly organize the administration system, a tray is provided with semi-cylindrical shaped longitudinal grooves which frictionally engage the barrels of the syringes, to restrict them from axial and lateral movement. The grooves are arranged parallel to one another and are variously dimensioned to accommodate syringes of various sizes. The tray is also provided with a lip or lateral groove having a surface which can abut a flange attached to one end of the syringe barrel to further restrict axial movement of the syringe barrel.

In the preferred embodiment, about eight longitudinal grooves are arranged in parallel sequence to accommodate syringes varying from 3 cc to 20 cc. In addition, an outer box protects the plungers of the syringes from being accidentally depressed.

A clamp means is attached to the tray or the accompanying outer box which permits the tray to be clamped onto a table supporting the patient. In this manner, the syringes are retained in a neat, orderly fashion at a position which is conveniently located near the head of the patient. A desired amount of any selected medication can quickly and easily be administered.

In another preferred embodiment, a second, similarly dimensioned box is arranged for clamping to the table at a convenient location or, alternatively, to be attached to the first outer box. The second box can contain miscellaneous equipment such as tape, scissors, clamps, spare syringes or medication, and the like, which may be required by the anesthesiologist during the surgery.

BRIEF DESCRIPTION OF THE DRAWING

The present invention will be more fully understood by reference to the following detailed description when read in conjunction with the accompanying drawing in which like reference characters refer to like parts throughout the several views, and in which:

FIG. 6 is an enlarged, detailed cross sectional view showing the second box clipped to the outer box;

FIG. 7 is a perspective view of an embodiment of the invention, shown in stacked arrangement with a lid;

FIG. 8 is a perspective view of another embodiment, showing the securing strap; and FIG. 9 is a perspective view of the securing strap, used to organize lines and tubes.

DETAILED DESCRIPTION OF THE PREFERRED EMBODIMENT

Figure 1:
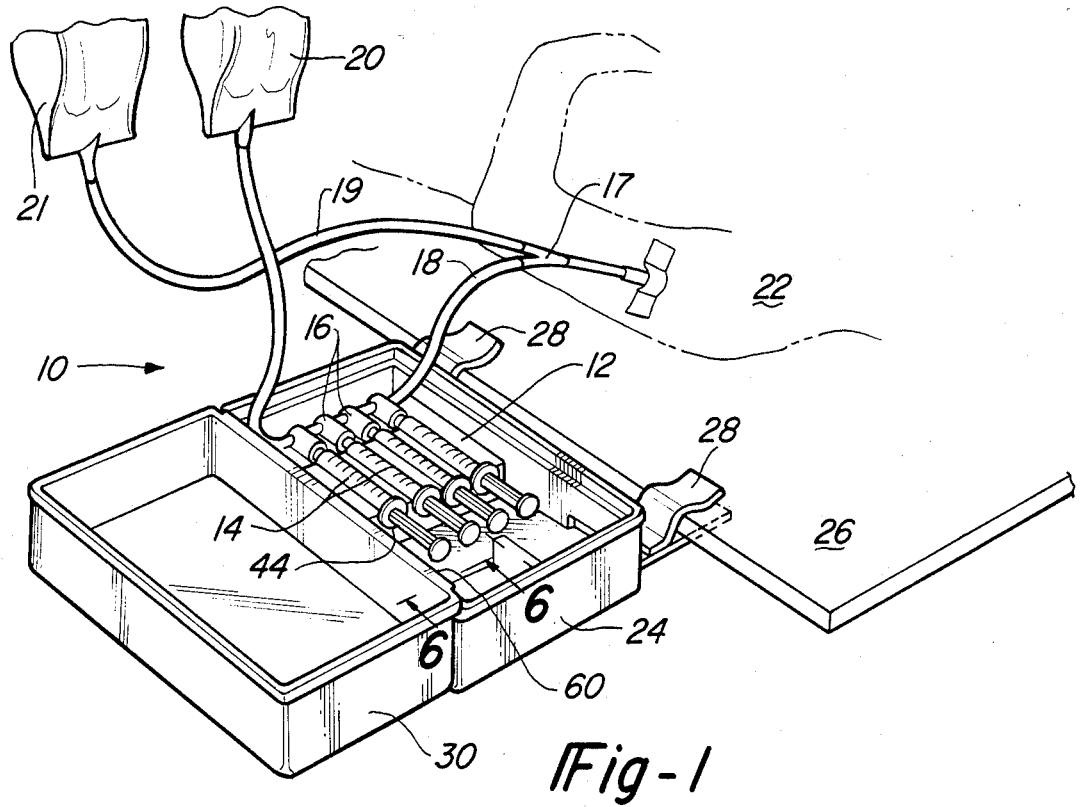
FIG. 1 is a perspective view of the preferred embodiment of the present invention, in use clamped to a table supporting a patient.

Referring first to FIG. 1, a preferred embodiment of the medication administration system 10 is thereshown comprising a tray 12, supporting syringes 14 which are connected to valves 16 in an auxiliary intravenous (IV) line 18 leading from an auxiliary source 20 of IV fluids to a side port 17 in a main IV line 19. The main IV line 19 leads from a main source 21 of IV fluids to a vein of a patient 22. The tray 12 is supported by a first or outer box 24 which is clamped to a table 26 by means of clamps 28. A second box 30 is shown attached to the first box 24 and may contain miscellaneous medical and/or anesthesiology equipment.

Referring now to FIGS. 2–5, the tray 12 and the outer box 24 are shown in more detail. The tray 12 and the outer box 24 may be molded as a single unit or, alternatively, the tray 12 is inserted in the interior of the box 24. The tray 12 and the box 24 may be made of any rigid material, such as molded plastic, so long as it is durable and can withstand repeated washing and disinfecting. The box 24 has two parallel sides, two ends, a bottom and an open top. The box 24 is approximatley 12 inches long, 10 inches wide and 2 inches deep but these dimensions can be varied within the scope of the invention.

Figure 2:
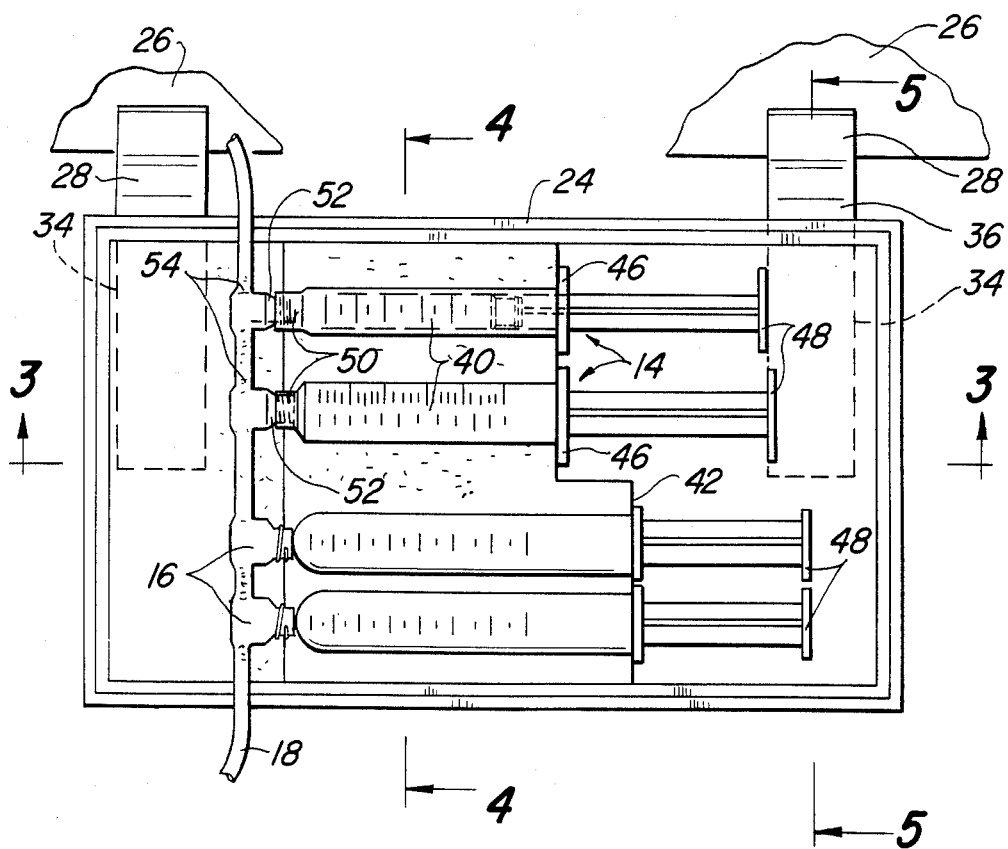
FIG. 2 is a top plan view of an embodiment of the medication administration system.
Figure 3:
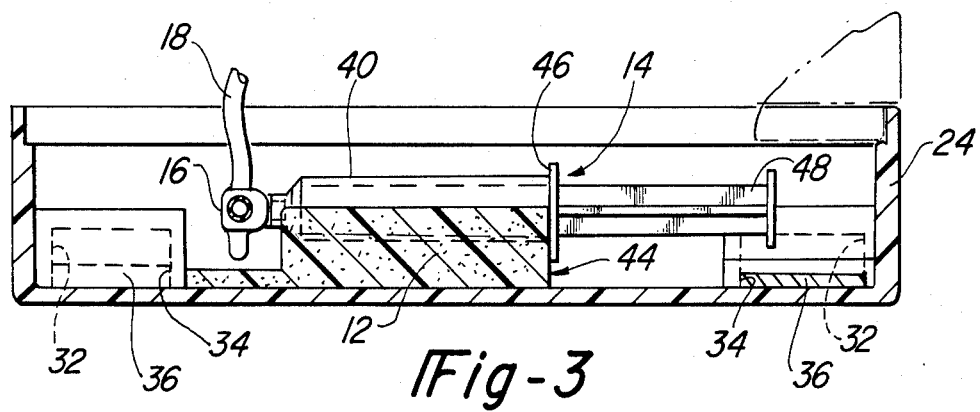
FIG. 3 is a longitudinal cross sectional view taken substantially along line 3—3 of FIG. 2.
Figure 4:
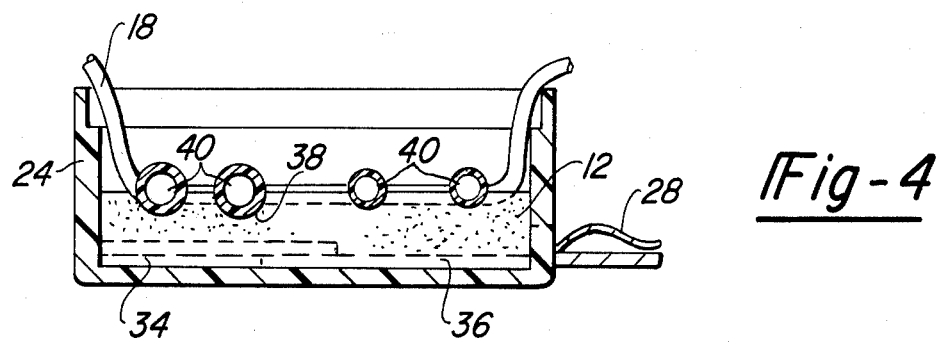
FIG. 4 is a lateral cross sectional view taken substantially along line 4—4 of FIG. 2.
Figure 5:
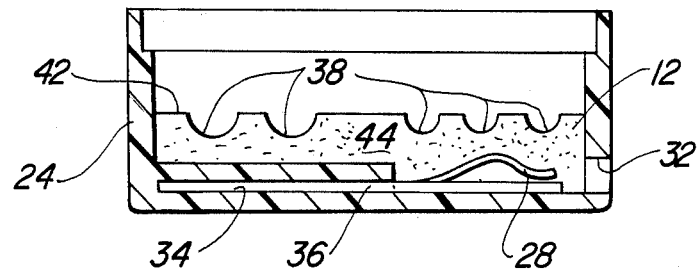
FIG. 5 is a lateral cross sectional view taken substantially along line 5—5 of FIG. 2.

One of the sides has two openings 32 (FIGS. 3 and 5) for a purpose which is to be described shortly. Two tracks 34 are disposed along the bottom of the tray 12 or the box 24 adjacent and parallel to each of the ends, and aligned with the openings 32. Each of the tracks 34 forms a guide for a sliding member 36 which supports the clamp 28. The clamp 28 and the sliding member 36 can be retracted into the box 24 through the opening 32 along the slide track 34. When the system 10 is to be used, the box 24 is secured to the table 26 by sliding the clamp 28 out of the box 24 and securing it to the table 26. Tabs or knobs (not shown) may be provided for sliding the clamps and locking them in position. The depth of the box 24 can be minimized by placing the tracks 34 at one end outside the valves 16 and, at the other end, outside the ends of the smaller syringes 14, as shown in FIG. 2.

Still referring to FIGS. 2–5, the tray 12 includes a plurality of semi-cylindrical longitudinal grooves 38. Although only four grooves 38 are shown in the drawing, it will be understood that the tray 12 may comprise any convenient number of grooves 38, and preferably contains eight. The grooves 38 are dimensioned to frictionally engage and securely grip the barrels 40 of the syringes 14. As it is desirable to use syringes 14 of various sizes, the grooves 38 must be dimensioned accordingly. For example, in the preferred embodiment having eight longitudinal grooves 38, two are dimensioned to engage the barrels of 20 cc syringes, one is dimensioned to engage the barrel of a 10 cc syringe, three grooves 38 are dimensioned to engage the barrels of 5 cc syringes, and two of the grooves 38 are dimensioned to engage the barrels of 3 cc syringes. Thus, as shown in the drawings, the grooves 38 have varying dimensions.

The frictional engagement between the barrels 40 and the grooves 38 prevents the syringes 14 from moving laterally or axially with respect to the tray 12. However, to further restrict axial movement of the syringes 14, a transverse groove or lip 42 is provided in the tray 12 and the lip 42 has a face 44 which abuts a flange 46 connected to the barrel 40 of the syringes 14. As the plunger 48 of the syringe 14 is depressed, any tendency of the barrel 40 to slide in the longitudinal groove 38 is prevented by abutment of the flange 46 against the face 44 of the tray 12. The flange 46 may be round as shown in the drawings, or any other shape, so long as a portion of the flange 46 abuts the face 44.

Although the grooves 38 of the tray 12 are the preferred embodiment for securing the syringes 14 against axial and lateral movement, other securing means are also contemplated by this invention. For example, the syringes 14 could be securely fastened to a planar surface such as a board with adhesive means such as tape. Alternatively, a leather or fabric member having pockets, or a strap having rings or loops, into which the syringes 14 can be inserted is also within the scope of the present invention. In yet another variation, semi-cylindrical grooves as described are provided with resilient members along their longitudinal edges which grip the syringe barrels 40.

Referring particularly to FIG. 2, the nozzles 50 of the syringe barrels 40 are secured to the inlets 52 of the valves 16. In this embodiment, each of the syringe nozzles 50 and the valves 16 are lined up approximately parallel to the ends of the box 24. Because syringes 14 of varying volumes have varying lengths as well, the grooves 38 must also have varying lengths. This requires that the lip 42 of the tray 12 be varied in a stepwise fashion as shown in FIGS. 2 and 7.

Each valve 16 comprises at least an inlet 52 and an outlet 54. The inlet 52 is fluidly connected to the nozzle 50 of a syringe 14, while the outlet 54 is in direct fluid communication with the IV line 18. The connections can be made by any means known in the art, such as screw threads, or lever locks. This direct connection provides a minimum amount of dead space between the outlet 54 and the IV line 18 to decrease the amount of medication which remains trapped in the intermediate tubing. Eliminating the dead space reduces the risk of precipitation caused by incompatible medications, and has the advantage of delivering an exact volume of medication to the patient 22.

The valves 16 may comprise manifolds having three way stop cocks which must manually be opened before medication can be delivered. Preferably, however, the valves 16 comprise one way valves or check valves which will freely permit flow from the inlet 52 to the outlet 54 but which will prevent any back flow. With the preferred one way valve 16, medication can be administered easily with one hand since it is unnecessary to open any valves.

It is to be understood that a valve 16 is associated with each groove 38. A syringe 14 may be associated with each valve 16 but this depends on the number of syringes 14 employed by the physician. It is possible, therefore, to have unused valves 16 in the system.

Referring now to FIGS. 1 and 6, the second box 30 is shown attached to the first box 24. The second box 30 is similar to the first box 24 in shape and construction and is attached to the first box 24 such as by means of a clip 60 which is formed in a U-shape and fits over the sidewall of the box 24. In this embodiment, a slot 62 (FIG. 6) is cut away from the tray 12 to receive the end 64 of the clip 60. Because of the weight of the equipment in the second box 30, the end 64 of the clip 60 must be relatively long, and must securely grip the wall of the first box 24. Alternatively, the boxes 24 and 30 may be connected by a hinge (not shown) of the type that permits complete separation of the boxes 24 and 30.

Additionally, as can best be seen in FIG. 1, the side of the second box 30 which is opposite the U-shaped clip 60 may be provided with openings 80, slide tracks 82, slide members 84 and the clamp members 86 which are substantially similar to the clamping means of the first box 24 and therefore will not be described in detail. Thus, the second box 30 may also be clamped to the table 26 at a convenient location.

Referring now to FIGS. 7 and 8, the boxes 24 and 30 are thereshown in a stacked arrangement, one on top of the other. The first box 24 may be dimensioned slightly smaller than the second box 30 or, alternatively, the end and sidewalls of each of the boxes may be slightly tapered so that the bottom of the boxes is slightly smaller than the open top. In this manner, the bottom of either box may be inserted into the top of the other box. It is also within the scope of this invention to invert one box on top of the other with a panel or flap inbetween to separate the contents of each box, or to place both boxes into a carrying case.

In addition a handle (not shown) can be placed on the top 70 or along the sides of the boxes 24, 30 for carrying the boxes to and from the operating room.

Also shown in FIGS. 7 and 8 is a lid 70 which comprises a substantially planar member which is slidable onto the open top of the outer box 24. By securely wrapping one or more straps 72 around the stacked boxes and lid 70, the entire system 10 may be stored neatly in an organized fashion. Preferably, the strap 72 comprises two portions each of which can be releasably secured to itself once it is wrapped around the boxes. For this purpose, one face of the strap 72 is provided with hook members 74 and the other face of the strap 72 is provided with corresponding loop members 76. In addition, when the system 10 is in use, one strap 72 may be fastened to the table 26 or to an IV pole doubled over upon the first strap 72 as shown in FIG. 9 to form loops 78 through which various cords, tubes or lines 80 may be passed to maintain them in an organized manner.

Having described the structural features of the present invention, its operation can be easily understood. The system 10 is particularly adapted for use by an anesthesiologist administering sedatives or anesthetics to the patient 22. Each anesthesiologist selects those medications which are indicated for the particular patient 22 and prepares the syringes 14 in advance with the amounts of the medications which he or she anticipates will be needed. Each syringe 14 may contain a different medication, or a medication which is used in large volume may occupy more than one syringe 14. The tray 12 containing the valves 16 is placed near the head of the patient 22. The valves 16 are connected to the auxiliary IV line 18 between the auxiliary source 20 and a side port 17 of the main IV line 19, leading to the patient 22. The nozzles 50 of the syringes 14 are connected to the inlets 52 of the valves 16 and the barrels 40 are pressed into place in the grooves 38 of the tray 12.

In putting the patient under the effect of sedatives or anesthetics, the anesthesiologist need only depress the plunger of the appropriate syringe 14 of the amount required to deliver a specific volume of medication. The volume delivered can be read from graduations on the side of the syringe barrel 40. Because of the operation of the one way valves 16, the anesthesiologist needs only one hand to deliver medication from the syringes 14, thereby freeing the other hand for additional care, such as maintaining the patient's airway. The syringes 14 are retained in position in the tray 12 and are restrained from axial or lateral movement. Moreover, the outer box 24 includes an end wall which provides protection against accidentially depressing a plunger and administering medication inadvertently. Thus, the system 10 provides a safety feature not found in the prior art.

The system 10 allows the anesthesiologist to administer as many as eight different medications in varying amounts conveniently and efficiently in a neat and organized fashion.

Moreover, the system 10 can be used by other physicians as well. For example, in chemotherapy several medications may be administered over a short time period and the system 10 of the present invention is easily adapted for this use.

The foregoing detailed description of the preferred embodiment has been given for clearness of understanding only and no unnecessary limitations should be understood therefrom. Some modifications will be obvious to those skilled in the art to which the invention pertains, without deviation from the spirit of the invention as defined by the scope of the appended claims.

I claim:

1. An administration system for administering selected medications to a patient, said system comprising:
   an intravenous line having one end adapted to be fluidly connected to a vein of the patient and another end adapted to be connected to a source of intravenous fluid;
   at least one syringe, having a barrel, a nozzle at one end of said barrel, a plunger and a longitudinal axis, and containing a selected medication;
   at least one valve means, having an inlet, an outlet and means for preventing flow from said outlet to said inlet, said valve means being arranged so that said outlet is in fluid communication with said intravenous line, and the nozzle of said at least one syringe is in fluid communication with the inlet of a corresponding one of said at least one valve means;
   securing means for releasably securing the barrel of said at least one syringe against axial and lateral movement;
   mounting means for removably mounting said means for selectively restraining at a convenient location near a patient;
   said securing means comprising a tray having at least one semi-cylindrical, longitudinal groove, dimensioned to receive and frictionally engage the barrel of said at least one syringe;
   said tray further comprising an outer box having an open top, a bottom and two parallel sides wherein said box supports said tray such that said at least one longitudinal groove is arranged parallel to the two sides and a space is provided between the tray and one end of the box for operation of the plunger;
   said mounting means comprising at least one clamp secured to said outer box and adapted for clamping onto a table supporting the patient; and
   said box further comprising track means disposed on an upper surface of said bottom, said clamp being slidably disposed on said track means and wherein said one side includes openings aligned with said track means so that said clamp can slide into the box for storage and out of the box through said openings for mounting the box.

2. The administration system as defined in claim 1 wherein said at least one valve means comprises a plurality of three-way stop cocks having a main inlet in addition to said inlet and outlet, said stop cocks being arranged in series to form a manifold, with the main inlet of a first stop cock being in fluid communication with the source of intravenous fluid, the outlet of a last stop cock being in fluid communication with the intravenous line to the patient, and the outlets of the first and intermediate stop cocks being in fluid communication with the main inlet of an adjacent stop cock;

each of said stop cocks further having means for selectively fluidly connecting said outlet to one of said main inlet and said inlet.

3. The administration system as defined in claim 1 wherein said at least one valve means comprises a plurality of one-way valves each having their outlets in direct fluid communication with said intravenous line such that there is substantially no dead space between said outlets and said intravenous line.

4. The administration system as defined in claim 1 wherein said at least one semi-cylindrical longitudinal groove comprises a plurality of semi-cylindrical, longitudinal grooves arranged substantially parallel to one another, and said at least one valve means comprises a corresponding plurality of valve means, one associated with each longitudinal groove so that said at least one syringe can engage one of said plurality of longitudinal grooves while being in fluid communication with the inlet of the associated valve.

5. The administration system as defined in claim 1 wherein the barrel of said at least one syringe has a flange disposed at an end thereof spaced from the nozzle, and wherein said tray further comprises a transverse lip formed at one end of said at least one longitudinal groove, said lip defining a surface against which said flange abuts to further restrict axial movement.

6. The administration system as defined in claim 1 wherein the number of said at least one longitudinal groove is 6–10.

7. The administration system as defined in claim 6 wherein the number of said longitudinal grooves is 8, and wherein two of said longitudinal grooves are dimensioned to receive 20 cc syringes, one longitudinal groove is dimensioned to receive a 10 c syringe, three longitudinal grooves are dimensioned to receive 5 cc syringes and 2 longitudinal grooves are dimensioned to receive 3 cc syringes.

8. The administration system as defined in claim 1 wherein said mounting means at least one clamp secured to said securing means and adapted for clamping onto a table supporting the patient; and said clamp means being slidably engable with said table.

9. The administration system as defined in claim 1 and comprising a second box for storing additional medical equipment, said second box comprising a second open top, a second bottom, two parallel second sides and two second ends, said second box being dimensioned slightly larger than said outer box so that the outer box may be inserted into said second box for stacked storage, said second box further comprising second mounting means for mounting the second box at a convenient location near the patient;

said second mounting means comprising a U-shaped clip disposed on one said second side, said clip being dimensioned to fit over one side of said outer box.

10. The administration system as defined in claim 9 and comprising a lid dimensioned to cover said outer box, and further comprising at least one belt having two faces, two sides and two ends, and having hook members disposed on one face and interacting loop members disposed on the other face, wherein said belt is dimensioned to wrap around and secure together said second box, said outer box and said lid when they are in a stacked arrangement by interacting said hook and loop members.

11. The administration system as defined in claim 1 wherein said tray is made of a durable, repeated washing and disinfecting resistant rigid plastics material.

12. An administration system for administering selected medications to a patient, said system comprising:

an intravenous line having one end adapted to be fluidly connected to a vein of the patient and another end adapted to be connected to a source of intravenous fluid;

at least one syringe, having a barrel, a nozzle at one end of said barrel, a plunger and a longitudinal axis, and containing a selected medication;

at least one valve means, having an inlet, an outlet and means for preventing flow from said outlet to said inlet, said valve means being arranged so that said outlet is in fluid communication with said intravenous line, and the nozzle of said at least one syringe is in fluid communication with the inlet of a corresponding one of said at least one valve means;

securing means for releasably securing the barrel of said at least one syringe against axial and lateral movement;

mounting means for removably mounting said means for selectively restraining at a convenient location near a patient;

said securing means comprising a tray having at least one semi-cylindrical, longitudinal groove, dimensioned to receive and frictionally engage the barrel of said at least one syringe;

said tray further comprising an outer box having an open top, a bottom, two parallel sides and two ends, wherein said box supports said tray such that said at least one longitudinal groove is arranged parallel to the two sides and a space is provided between the tray and one end of the box for operation of the plunger;

said mounting means comprising at least one clamp secured to said outer box and adapted for clamping onto a table supporting the patient;

said at least one clamp comprises two clamps disposed on one side of said box adjacent each end; and said box further comprising two tracks disposed on an upper surface of said bottom adjacent and parallel to said ends, said clamps being slidably disposed on said tracks, and wherein said one side includes openings aligned with said tracks so that said clamps can slide into the box for storage and out of the box through said openings for mounting the box.

13. An administration system for administering selected medications to a patient, said system comprising:

an intravenous line having one end adapted to be fluidly connected to a vein of the patient and another end adapted to be connected to a source of intravenous fluid;

at least one syringe, having a barrel, a nozzle at one end of said barrel, a plunger and a longitudinal axis, and containing a selected medication;

at least one valve means, having an inlet, an outlet and means for preventing flow from said outlet to said inlet, said valve means being arranged so that said outlet is in fluid communication with said intravenous line, and the nozzle of said at least one syringe is in fluid communication with the inlet of a corresponding one of said at least one valve means;

securing means for releasably securing the barrel of said at least one syringe against axial and lateral movement;

mounting means for removably mounting said means for selectively restraining at a convenient location near a patient;

said securing means comprising a tray having at least one semi-cylindrical, longitudinal groove, dimensioned to receive and frictionally engage the barrel of said at least one syringe;

said tray further comprising an outer box having an open top, a bottom, two parallel sides and two ends, wherein said box supports said tray such that said at least one longitudinal groove is arranged parallel to the two sides and a space is provided between the tray and one end of the box for operation of the plunger;

said system further comprising a second box for storing additional medical equipment, said second box comprising a second open top, a second bottom, two parallel second sides and two second ends, said second box being dimensioned slightly larger than said outer box so that the outer box may be inserted into said second box for stacked storage, said second box further comprising second means for mounting the second box at a convenient location near the patient; and said second box further comprising two second tracks disposed on an upper surface of said second bottom adjacent and parallel to said second ends, one second side having second openings aligned with each second track, and wherein said second means for mounting comprises two second clamps slidably disposed on said second tracks so that said second clamps can slide into said second box for storage and out of said second box through said second openings for mounting the second box.

* * * * *